United States Patent [19]

Eberlein et al.

[11] Patent Number: 4,724,236
[45] Date of Patent: Feb. 9, 1988

[54] 5,11-DIHYDRO-6H-PYRIDO(2,3-B)(1,4)BENZODIAZEPIN-6-ONES SUBSTITUTED IN THE 11-POSITION, PROCESSES FOR PREPARING THEM AND PHARMACEUTICAL COMPOSITIONS CONTAINING THESE COMPOUNDS

[75] Inventors: Wolfgang Eberlein, Biberach; Günter Trummlitz, Warthausen; Wolfhard Engel; Gerhard Mihm, both of Biberach; Rudolf Hammer, Ingelheim am Rhein; Norbert Mayer, Biberach, all of Fed. Rep. of Germany; Antonio Giachetti, Mailand, Italy; Adriaan de Jonge, Biberach, Fed. Rep. of Germany

[73] Assignee: Karl Thomae GmbH, Riss, Fed. Rep. of Germany

[21] Appl. No.: 944,146

[22] Filed: Dec. 19, 1986

Related U.S. Application Data

[63] Continuation of Ser. No. 875,436, Jun. 17, 1986, abandoned.

[30] Foreign Application Priority Data

Jun. 27, 1985 [DE] Fed. Rep. of Germany ....... 3523002
Apr. 3, 1986 [DE] Fed. Rep. of Germany ....... 3611097

[51] Int. Cl.$^4$ ............... A61K 31/55; C07D 471/04; C07D 403/14
[52] U.S. Cl. .................................... 514/215; 540/495
[58] Field of Search ................... 540/495; 514/215

[56] References Cited

U.S. PATENT DOCUMENTS 4,308,206 12/1981 Gerzberg .................... 540/495

Primary Examiner—Robert T. Bond
Attorney, Agent, or Firm—David E. Frankhouser; Alan R. Stempel; Mary-Ellen M. Timbers

[57] ABSTRACT

Compounds of general formula I are described,

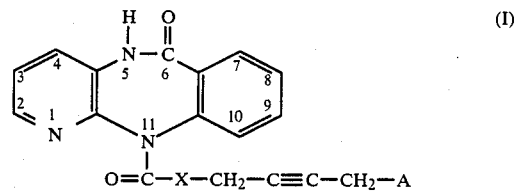

wherein
X represents the group =CHR, =NR or an oxygen atom and
A represents the groups —NR$^1$R$^2$,
wherein R$^1$ and R$^2$ represent alkyl, cycloalkyl or phenylalkyl groups, n represents the number 0, 1 or 2, R$^3$ represents a hydrogen atom, a hydroxy or alkyl group or a group —(CH$_2$)$_n$—N—R$^5$R$^6$ (R$^5$ and R$^6$ being lower alkyl groups) and R$^4$ is an alkyl or phenylalkyl group; two processes for preparing these compounds and the salts thereof are also described.

The compounds have favourable effects on heart rate and can be used as vagal pacemakers for treating bradycardia and bradyarrhythmia in human and veterinary medicine. Some of these compounds also have very good antithrombotic effects.

8 Claims, No Drawings

5,11-DIHYDRO-6H-PYRIDO(2,3-B)(1,4)BENZODIAZEPIN-6-ONES SUBSTITUTED IN THE 11-POSITION, PROCESSES FOR PREPARING THEM AND PHARMACEUTICAL COMPOSITIONS CONTAINING THESE COMPOUNDS

This is a continuation of application Ser. No. 875,436, filed June 17, 1986, now abandoned.

The invention relates to new 5,11-dihydro-6H-pyrido[2,3-b][1,4]benzodiazepin-6-ones substituted in the 11-position, the pharmacologically acceptable salts thereof with inorganic or organic acids, processes for preparing them and pharmaceutical compositions containing these compounds.

Condensed diazepinones with anti-ulcerative properties and inhibiting properties on the secretion of gastric acid are already known from EP-A Nos. 0 039 519 and 0 057 428 and from U.S. Pat. Nos. 3,660,380, 3,691,159, 4,213,984, 4,213,985, 4,210,648, 4,410,527, 4,424,225, 4,424,222 and 4,424,226.

It has now been found that the diazepinones according to the invention having novel substituents in the 11-position surprisingly have valuable pharmacological properties completely different from those of the compounds of the above-mentioned publications.

The compounds according to the invention have the general formula I

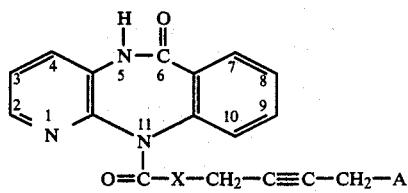

wherein
X represents the groups

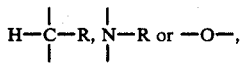

and
A represents the groups

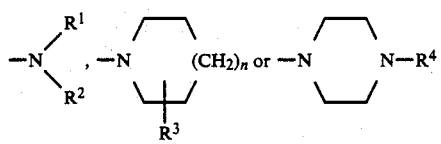

wherein
R represents a hydrogen atom or an alkyl group with 1 to 3 carbon atoms,
$R^1$ and $R^2$, which may be identical or different, represent a hydrogen atom, an alkyl group with 1 to 3 carbon atoms, a phenylalkyl group with a total of 7 to 9 carbon atoms, a 5 to 7 membered cycloalkyl group optionally substituted by a hydroxy group,
n represents the number 0, 1 or 2, $R^3$ represents a hydrogen atom, a hydroxy group, an alkyl group with 1 to 3 carbon atoms or a group of formula

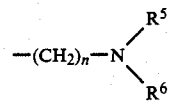

wherein
n is defined as hereinbefore, and $R^5$ and $R^6$ represent an alkyl group with 1 to 3 carbon atoms, and
$R^4$ represents a straight-chained or branched alkyl group with 1 to 3 carbon atoms or a phenylalkyl group with a total of 7 to 9 carbon atoms.

The compounds of general formula I may also be present in the form of the physiologically acceptable salts thereof after reaction with inorganic or organic acids. Suitable acids include, for example, hydrochloric, hydrobromic, sulfuric, methylsulfuric, phosphoric, tartaric, fumaric, citric, maleic, succinic, malic, p-toluenesulfonic, methanesulfonic or amidosulfonic acid.

According to the invention the compounds of general formula I are obtained by the following processes:

(a) by reacting a compound of general formula II

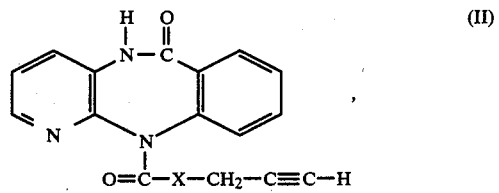

wherein
X is as hereinbefore defined, with amines of formula

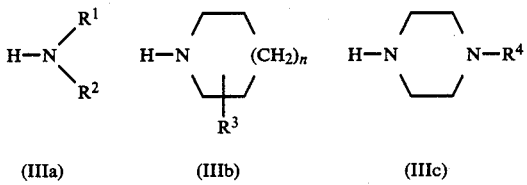

wherein
$R^1$, $R^2$, $R^3$ and $R^4$ are as hereinbefore defined, or with the salts thereof in the presence of formaldehyde or paraformaldehyde and, optionally,
in the presence of catalytic quantities of salts such as copper(I) chloride of iron(II) chloride. The salts of the amines of formulae IIIa, IIIb and IIIc used are preferably the halides, e.g. the hydrochlorides, or the acetates thereof.

The reaction is carried out in an organic solvent at temperatures up to the boiling point of the reaction mixture. Suitable solvents include cyclic ethers such as dioxan and alcohols such as ethyl alcohol. When dioxan is used it is advisable to add acetic acid. The reaction may be accelerated by the addition of salts such as copper(I) chloride or iron(II) chloride. Generally, the formaldehyde or paraformaldehyde is first combined with an amine of formula IIIa, IIIb or IIIc or a salt thereof, e.g. a hydrochloride or an acetate thereof, in the solvent and only then is the compound of general formula II added. After the mixture has been heated to reflux temperature, the insoluble matter is filtered off and the end product is isolated in the conventional manner. The procedures conventionally used for Mannich reactions apply (cf. Weygand and Hilgetag, "Organisch-Chemische Experimentierkunst", pages 990 et seq.).

(b) Compounds of general formula I wherein X is the group

with the meanings given for R above, may also be prepared by reacting the dilithium salt of the compound of formula IV

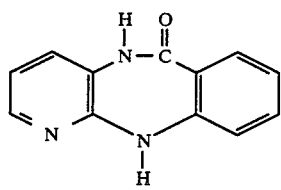
(IV)

with an ester of general formula V

A—CH$_2$—C≡C—CH$_2$—CHR—COOR$^7$  (V)

wherein A and R are as hereinbefore defined and R$^7$ represents an alkyl group with 1 to 10 carbon atoms, a phenylalkyl group with a total of 7 to 10 carbon atoms or a phenyl group.

The 5,11-dihydro-6H-pyrido[2,3-b][1,4]benzodiazepin-6-one of formula IV is converted into the dilithium salt thereof by means of lithium alkyls but particularly with n-butyl-lithium, n-butyl-lithium in the presence of tetramethylethylenediamine, tert.butyl-lithium, lithium diisopropylamide or lithium dicyclohexylamide or with lithium aryls, e.g with phenyl-lithium. Conversion into the lithium salt and further reaction to obtain the end product are effected in an organic solvent at temperatures of between −60° C. and +20° C., but preferably at −10° C. The organic solvents used are those conventionally used for reaction with lithium reagents; it is particularly advantageous to use tetrahydrofuran or other ethers such as diethylether, aliphatic hydrocarbons such as hexane or mixtures thereof, optionally also in the presence of hexamethyl phosphoric acid triamide as co-solvent. Shortly after the addition of the metallisation reagent has ended, a stoichiometric quantity or slight excess of the ester of general formula V is added and the reaction mixture is allowed slowly to reach ambient temperature, e.g. over a period of 2 hours, in order to complete the reaction. The compound of formula I formed is isolated from the reaction mixture by conventional methods and the free compound is obtained, which may subsequently be converted into the salts thereof if desired.

The compounds of formula I obtained by this process may subsequently be converted into the acid addition salts thereof or, if acid addition salts are obtained, these may be converted into the free bases or into other pharmacologically acceptable acid addition salts using methods known per se.

If, according to the processes described above compounds of general formula I are obtained wherein X represents the group >CHR with the meanings for R given hereinbefore, with the exception of a hydrogen atom, or wherein A represents a group with the radical R$_3$ whilst R$_3$ has the meanings given hereinbefore, with the exception of a hydrogen atom, these compounds may occur in diastereomeric forms or as enantiomeric (+) and (−) forms. The invention includes the individual isomers and the mixtures thereof. The diastereomers may be separated on the basis of their different physicochemical properties, e.g. by fractional recrystallization from suitable solvents, by high pressure liquid chromatography, column chromatography or gas-chromatographic methods.

The resolution of any racemates of the compounds of general formula I may be carried out by known methods, for example, using an optically active acid such as (+) or (−) tartaric acid or a derivative thereof such as (+) or (−) diacetyltartaric acid, (+) or (−) monomethyltartrate or (+) camphorsulfonic acid.

According to a conventional method of isomer separation, the racemate of general formula I is reacted with one of the above-mentioned optically active acids in equimolar quantities in a solvent and the crystalline optically active salts obtained are separated on the basis of their different solubilities. This reaction may be carried out in any type of solvent provided that the solvent presents a sufficient difference in solubility of the salts. Preferably, methanol, ethanol or mixtures thereof, for example in a volume ratio of 50:50, are used. Then each of the optically active salts is dissolved in water, neutralized with a base such as sodium carbonate or potassium carbonate and in this way the corresponding free compound is obtained in the (+) or (−) form.

Only one enantiomer or a mixture of two optically active diastereomeric compounds covered by general formula I will be obtained if the methods of synthesis described above are carried out with structurally defined starting compounds.

The starting compounds of general formula II wherein
X represents the group

with the meanings given for
R hereinbefore are prepared by reacting the dilithium salt of 5,11-dihydro-6H-pyrido[2,3-b][1,4]benzodiazepin-6-one with a pentynoic acid halide of general formula VI

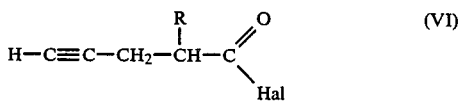
(VI)

wherein
R is as hereinbefore defined and Hal represents a halogen atom, preferably a chlorine or bromine atom. The 5,11-dihydro-6H-pyrido[2,3-b][1,4]benzodiazepin-6-one is converted into the dilithium salt using lithium alkyls, but particularly using n-butyl-lithium, n-butyl-lithium in the presence of tetramethylethylenediamine, tert.butyl-lithium, lithium diisopropylamide or lithium dicyclohexylamide or with lithium aryls, e.g. with lithium phenyl. Conversion into the lithium salt and further reaction to obtain the end product are effected in an organic solvent at temperatures of between −60° C. and +20° C., but preferably at −10° C. The organic solvents used are those conventionally used for reactions with lithium reagents; it is particularly advantageous to use tetrahydrofuran or other ethers such as diethylether, or aliphatic hydrocarbons such as hexane, or mixtures thereof, optionally in the presence of hexamethylphosphoric acid triamide as co-solvent. Shortly after the addition of the metallisation reagent has ended, the stoichiometric quantity or a slight excess of the acid halide of general formula VI is added and the reaction mixture is allowed to come slowly to ambient temperature, e.g. within 2 hours, in order to complete the reaction. The compound of formula II formed is isolated from the reaction mixture by conventional methods and then, if desired, converted into the salts thereof.

An acid halide of general formula VI may be prepared from the corresponding 4-pentynoic acid by reacting with a thionyl halide. The 4-pentynoic acids are prepared by methods known per se. 2-Methyl-4-pentynoic acid is obtained, for example, by the method described in Bull. Soc. Chim. France, 1954, pages 797 and 798, starting from diethyl methylmalonate.

The starting compounds of general formula II wherein
X represents the group

with the definitions given from R hereinbefore are prepared by reacting pyridobenzodiazepinones of general formula VII

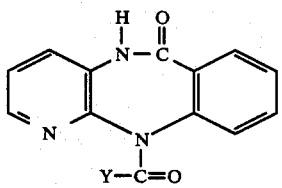 (VII)

wherein
Y represents a halogen atom, preferably a chlorine or bromine atom, with the amine of general formula VIII

H—C≡C—CH$_2$NH—R    (VIII)

wherein
R is defined as hereinbefore. The reaction is preferably carried out in the presence of solvents, e.g. water, toluene, alcohols such as methanol, ethanol, propanol, but preferably in the presence of aprotic polar solvents such as tetrahydrofuran, 1,4-dioxan, acetonitrile, N,N-dimethylformamide, dimethylsulfoxide, hexamethylphosphoric acid triamide or mixtures thereof and at temperatures of between 0° C. and the boiling point of the reaction mixture, preferably between 40° and 100° C. It is advantageous to add an inorganic or organic base such as sodium hydroxide, triethylamine or pyridine or an excess of the base of general formula VIII.

The starting compounds of general formula II wherein
X is an oxygen atom are prepared by reacting a pyridobenzodiazepinone of general formula VII with the compound of formula IX H—C≡C—CH$_2$OLi    (IX).

The reaction is preferably carried out in water or ethanol, propanol, n-hexane or in aprotic polar solvents such as tetrahydrofuran, at temperatures up to the boiling point of the reaction mixture. The compound of formula IX is advantageously produced in situ by reacting propynol with a stoichiometric quantity of n-butyl-lithium or phenyl-lithium, which may be immediately followed by reaction with the pyridobenzodiazepinone of general formula VII.

The compounds of general formulae IIIa, IIIb, IIIc, and VIII are known from the literature or may be prepared analogously to methods known from the literature.

The compounds of general formula VII needed as intermediate products are obtained by reacting the 5,11-dihydro-6H-pyrido[2,3-b][1,4]benzodiazepin-6-one of formula IV with a halocarbonic acid derivative of general formula X

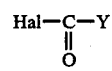 (X)

wherein Hal and Y, which need not be identical to one another, represent a chlorine or bromine atom. The reaction is carried out in inert solvents, e.g. in aromatic hydrocarbons such as toluene, chlorobenzene, xylene, open-chained or cyclic ethers such as diisopropylether, tetrahydrofuran or dioxan, in ketones such as 3-pentanone, or in other solvents such as acetonitrile or dimethylformamide, preferably in the presence of tertiary organic bases such as pyridine, at temperatures up to the boiling point of the reaction mixture, but preferably between 30° and 80° C.

The preparation of the 5,11-dihydro-6H-pyrido[2,3-b][1,4]-benzodiazepin-6-one of formula IV is described in U.S. Pat. No. 3,406,168.

The invention further relates to pharmaceutical compositions which contain one or more compounds of general formula I or the physiologically acceptable salts thereof.

For this purpose, the compounds of general formula I may be incorporated in a manner known per se in the usual pharmaceutical preparation forms, e.g. solutions, suppositories, tablets, coated tablets, capsules or infusions. The daily dosage is generally between 0.02 and 5 mg/kg, preferably between 0.2 and 1.0 mg/kg of body weight, optionally administered in the form of several dosage units, preferably 1 to 3 doses, in order to obtain the desired results.

The basically substituted condensed diazepinones of general formula I and the acid addition salts thereof have valuable properties; in particular, they have favourable effects on heart rate and, owing to the fact that they do not inhibit salivation or have any mydriatic effects, they are suitable as vagal pacemakers for treating bradycardia and bradyarrhythmia in human and veterinary medicine; some of the compounds also demonstrate spasmolytic effects on peripheral organs, particularly the colon and bladder.

Moreover, some of the compounds showed bleeding time-prolonging properties on mice and rats when tested by the test designed by W. W. Duke, J. Amer. Med. Ass. 15, 1185 (1910) and antithrombotic properties in rats in the test designed by Poliwoda et al., (cf page 18) when administered in doses of between 0.1 and 10 mg/kg after intravenous and oral administration, respectively.

A favourable correlation between tachycardiac effects on the one hand and the undesirable effects on pupil size and the secretion of tears, saliva and gastric acid which occur with therapeutic compositions having anticholinergic activity components, on the other hand, is particularly important for the therapeutic use of the substances. The following tests show that the compounds according to the invention have surprisingly good correlations of this kind.

A. Test of functional selectivity of the anti-muscarinic effect

Substances with antimuscarinic properties inhibit the effects of exogenically supplied agonists or acetylcholine which is released from cholinergic nerve endings. The following is a description of methods suitable for determining cardioselective antimuscarinic agents.

The methods used had the objective of confirming the selectivity of the antimuscarinic activity.

The substances 5,11-dihydro-11-[1-oxo-6-(1-piperidinyl)-4-hexynyl]-6H-pyrido[2,3-b][1,4]benzodiazepin-6-one=A and
5,11-dihydro-11-[1-oxo-6-(hexahydro-1H-azepin-1-yl)-4-hexynyl]-6H-pyrido[2,3-b][1,4]benzodiazepin-6-one=B were tested for their 1. tachycardiac effect in conscious dogs,
2. inhibition of salivation stimulated by oxotremorin in the rat and
3. Mydriatic activity in the rat.

1. Heart rate-increasing activity in the conscious dog

The substances were injected intravenously and the heart rate was recorded using a tachygraph. After a control interval, increasing doses of the compound were administered in order to increase the heart rate. The next dose was injected when the effect of the preceding dose was no longer visible. The dosage of a substance which brought about an increase of 50 beats/minute ($ED_{50}$) was determined graphically. Each substance was tested on 3 to 5 dogs.

2. Inhibition of salivation in the rat 10 female albino rats (strain Crl:COBS-CD (SD) BR) having a body weight from 120 to 150 g, were used for each treatment group, and 24 hours before the start of the test the rats were deprived of food but given free access to drinking water.

In order to determine the muscarinic effect of oxotremorin on each of the symptoms being investigated in preliminary tests, a dosage-activity curve was drawn up with at least 3 dosages for each symptom.

When testing antimuscarinic substances, the oxotremorin dose used was that which had triggered the symptom to be influenced in 90 to 100% of the animals in the preliminary test 5.

Secretion of saliva: 0.083 mg/kg i.v.

Each antimuscarinic substance was administered intravenously in uniformly graduated dosages 15 minutes before the administration of oxotremorin. Control groups were given the solvent and suspension agent in corresponding amounts instead of the test substance.

Immediately after the administration of oxotremorin the animals were observed in a glass cage for 15 minutes.

The test for influence on oxotremorin-induced saliva secretion was carried out as a blind test, i.e. the investigator did not know which preliminary treatment the animals had received.

The results were expressed as the percentage inhibition of the oxotremorin effect (percentage of animals without the symptom in question). $ED_{50}$ values were determined by the method of LITCHFIELD and WILCOXON (J. Pharmacol. Exp. Ther. 96, 99, 1949).

3. Mydriatic effect on the rat

The mydriasis was determined by measuring the increase in pupil size after intravenous injection of the test substance. The pupil size was measured with a microscope. The measurements were taken before and at various times (15, 45 and 75 minutes) after the injection of different doses of the substance. The results were expressed as the $ED_{200}$. That is the dose which doubled the diameter of the pupil, compared with the basal value. The maximum effect was usually observed between 15 and 45 minutes after intravenous administration.

B. Studies of binding to muscarinic receptors: determining the $IC_{50}$ value

Male Sprague-Dawley rats weighing from 180–220 g served as organ donors. After the heart, stomach and cerebral cortex had been removed, all other procedures were carried out in ice-cold Hepes-HCl buffer (pH 7.4; 100 m molar NaCl, 10 m molar $MgCl_2$). The whole heart was cut up with scissors. All the organs were then homogenised in a Potter apparatus.

For the binding test the homogenised organs were diluted as follows:

Whole heart 1:250

Cerbral cortex 1:3000

The homogenised organs were incubated at a specific concentration of the radioactive ligand and a series of concentrations of the non-radioactive test substances in an Eppendorf centrifugal test tube at 30° C. The period of incubation was 45 minutes. 0.3 micro-mol of $^3$H-N-methylscopolamine ($^3$H-NMS) was used as the radioactive ligand. After incubation had been ended by centrifuging at 14000 g, the radioactivity in the pellet was determined. It represents the sum of specific and non-specific binding of $^3$H-NMS. The proportion of non-specific binding was defined as the radioactivity which was bound in the presence of 1 micro-mol of quinuclidinyl benzylate. Fourfold measurements were taken in each case. The $IC_{50}$ values of the non-labelled test substances were determined graphically. They represent the concentration of test substance at which the specific binding of $^3$H-NMS to the muscarinic receptors in the various organs was inhibited by 50%.

Results

TABLE I

Tachycardiac effects on the conscious dog, inhibition of oxotremorin stimulated salivation in the rat and mydriatic effect in the rat:

| Substance | Tachycardia (dog) $ED_{50}$ [micro g/kg] i.v. | Inhibition of salivation (rat) $ED_{50}$ [micro g/kg] i.v. | Mydriasis (rat) $ED_{50}$ [micro g/kg] i.v. |
|---|---|---|---|
| A | 44 | 2048 | ~3000 |
| B | 28 | 1136 | 2189 |

TABLE II

Studies of binding to muscarinic receptors, determining the $IC_{50}$ value:

| Substance | Receptor binding test $IC_{50}$ [nM] | |
|---|---|---|
| | Cortex | Heart |
| A | 1200 | 120 |
| B | 220 | 30 |

The pharmacological data in Table I above show that the heart rate is increased by the compounds mentioned even at dosages at which no restriction of salivation and no mydriasis are observed.

The data in Table II above, show that the new compounds of formula I distinguish between muscarinic receptors in different tissues. This is clear from the considerably higher $IC_{50}$ values in tests on preparations from the cerbral cortex compared with those from the heart.

Some of these compounds of formula I and the acid addition salts thereof also surprisingly have a powerful antithrombotic activity, as mentioned hereinbefore. This is clearly shown by the effect on platelet clots in rats by the substance 5,11-dihydro-11-[1-oxo-2-methyl-6-(4-methyl-1-piperazinyl)-4-hexinyl]-6H-pyrido[2,3-b][1,4]benzodiazepin-6-one=C which was used in the form of its dihydrochloride in the tests. These tests will now be described.

Effect on platelet clots in the rats

Essentially the method described by Poliwoda, Lilli, Hagemann, Schyma, in Z. ges. exp. Med. 145, 252, (1968) was used.

Method:

Male SPF rats (Chbb:THOM) weighing from 70 to 90 g, given free access to food (Altromin ®), and water up until the start of the test, were anaesthetised with Nembutal administered by intraperitoneal route (50 to 60 mg/kg of pentobarbital-Na). In order to avoid hypothermia they were kept on a heated test bench (37° C.).

After the abdomen had been opened up with a transverse cut the loop of small intestine was taken out and fixed and a mesenterial vein with a diameter of 300 microns was placed under a binocular operation microscope with ×40 magnification. A monopolar V4A steel electrode embedded in glass, with a diameter of 100 microns at the tip, was applied to the vein as stimulating cathode. The anode was applied to the same vessel opposite the cathode. Stimulation was effected with 150 volts of direct current for a period of 100 microsec. After stimulation, the observation area was continuously rinsed with warm (37° C.) physiological saline solution.

The formation and growth of the clot was monitored under the microscope over a period of 20 minutes. Throughout the entire observation period, the percentage narrowing of the diameter of the vessel by the clot was determined and noted initially at 10 second intervals and later every minute. The results were recorded in terms of time in a coordinate system. The area under the curve thus obtained constitutes a measurement of the size of the clot with time.

A group of 5 animals were given, 5 minutes before the start of observation, 1 mg/kg of substance C in the form of the dihydrochloride by intravenous route (0.1 ml per 100 g of body weight, solvent distilled water). A control group, also consisting of 5 animals, was given the carrier by intravenous route, the treatment being otherwise identical.

The area under the curve of the animals treated with the test substance was compared with that of the control animals. The reduction of the size of the clot under the influence of the substance was determined as the percentage reduction in the average value of the area under the curve of the substance-treated animals over the entire observation period compared with the average value of the controls.

The significance of the reduction was calculated by Student's t test for independent random samples (CAVALLI-SFORZA: Biometrie, G. Fischer-Verlag, Stuttgart 1969, page 72).

Results:

| Treatment | Dosage mg/kg i.v. | n | Substance C "area under curve" units of area average ± SD | percentage reduction compared with controls |
|---|---|---|---|---|
| Control | — | 5 | 1736.0 ± 124.2 | |
| Substance C in form of dihydrochloride | 1 | 5 | 1230.0 ± 188.0[x] | 29.2 |

[x]significant reduction, t test, p < 0.02.

The dihydrochloride of Substance C administered in a dosage of 1 mg/kg i.v., reduces the size of the electrically induced mesenterial clots in rats by a highly significant amount, namely 29.2%. It was thus surprisingly found that this substance has a marked antithrombotic activity.

Moreover, the compounds prepared according to the invention are well tolerated and even at the highest doses administered in the pharmacological test no toxic side effects were observed.

The following Examples are intended to illustrate the invention:

Preparation of starting materials

EXAMPLE A 5,11-Dihydro-11-[1-oxo-4-pentynyl]-6H-pyrido[2,3-b][1,4]-benzodiazepin-6-one 22.4 ml of a 1.6 molar solution of n-butyl-lithium in n-hexane are added dropwise with stirring, at 0° C., to a suspension of 3.7 g (0.017 mol) of 5,11-dihydro-6H-pyrido[2,3-b][1,4]benzodiazepin-6-one in 150 ml of absolute tetrahydrofuran. After it has all been added, the mixture is stirred for a further 30 minutes and then mixed with a solution of 2.04 g (0.0175 mol) of 4-pentynoic acid chloride in 20 ml of tetrahydrofuran. The mixture is heated to 30° C. and stirred for a further hour. The reaction mixture is then poured into a saturated saline solution. The organic phase is diluted with ethyl acetate and, after being separated off, washed twice with saline solution, filtered over charcoal and evaporated to dryness in vacuo. The crude product is purified by column chromatography on silica gel using chloroform as eluant. 2.2 g (43% of theory) of colourless crystals were obtained, melting point 179°–180° C.

EXAMPLE B 5,11-Dihydro-11-[2-methyl-1-oxo-4-pentynyl]-6H-pyrido[2,3-b][1,4]benzodiazepin-6-one Analogously to Example A, using 63 g (0.3 mol) of 5,11-dihydro-6H-pyrido[2,3-b][1,4]benzodiazepin-6-one and 46.8 g (0.36 mol) of 4-(2-methyl)-pentynoic acid chloride, 88 g (96% of theory) of the desired compound were obtained, m.p. 202°–204° C.

EXAMPLE C 5,11-Dihydro-11-[[(2-propynyl)-amino]carbonyl]-6H-pyrido[2,3-b][1,4]benzodiazepin-6-one 5.5 g (0.1 mol) of propargylamine were added dropwise with stirring at ambient temperature to a suspension of 27.3 g (0.1 mol) of 11-chlorocarbonyl-5,11-dihydro-6H-pyrido[2,3-b][1,4]benzodiazepin-6-one and 10.0 g (0.1 mol) of triethylamine in 500 ml of chloroform, whereupon the temperature rises to 35° C. The mixture is stirred for a further 30 minutes at 40° C., then filtered over activated charcoal and the reaction solution is evaporated to dryness in vacuo. After the oily residue has been decocted with ethyl acetate the desired product is obtained in the form of a colourless crystalline mass in a yield of 20.7 g (71% of theory).

EXAMPLE D 5,11-Dihydro-11-[[N-methyl(2-propynyl)amino]carbonyl]-6H-pyrido[2,3-b][1,4]benzodiazepin-6-one Analogously to Example C, using 27.3 g (0.1 mol) of 11-chlorocarbonyl-5,11-dihydro-6H-pyrido[2,3-b][1,4]benzodiazepin-6-one and 7.0 g (0.1 mol) of N-methyl-propargylamine, 27 g (88% of theory) of the desired compound are obtained.

EXAMPLE E 5,11-Dihydro-11-[[(2-propynyl)oxy]carbonyl]-6H-pyrido[2,3-b][1,4]benzodiazepin-6-one At 15° to 20° C., 3.08 g (0.048 mol) of n-butyl-lithium in 30 ml of n-hexane are added dropwise to a solution of 2.24 g (0.04 mol) of propargyl alcohol in 120 ml of tetrahydrofuran. After it has all been added, the mixture is stirred for a further 30 minutes at ambient temperature and then mixed with a suspension of 10.9 g (0.04 mol) of 11-chlorocarbonyl-5,11-dihydro-6H-pyrido[2,3-b][1,4]benzodiazepin-6-one in 250 ml of tetrahydrofuran. In order to complete the reaction the mixture is stirred for a further hour. It is evaporated to dryness in vacuo and the residue is crystallised by stirring in water. After recrystallisation from ethyl acetate, 7.5 g (64% of theory) of the desired product are obtained, m.p. 213° C.

EXAMPLE F 5,11-Dihydro-11-[1-oxo-2-methyl-4-pentynyl]-6H-pyrido[2,3-b][1,4]benzodiazepin-6-one (a) Diethyl 2-methyl-2-propargyl-malonate At 35° to 40° to C., with stirring, 174 g (1.0 ml) of diethyl methylmalonate are added dropwise to an alkoxide solution (prepared from 23 g of sodium and 800 ml of absolute ethanol), the mixture is stirred for a further hour and then at 45° C. 130.8 g (1.1 mol) of propargyl bromide are added dropwise. The mixture is refluxed for a further 2 hours. After cooling the precipitated sodium bromide is separated by suction filtering and the filtrate is substantially evaporated in vacuo. The residue is stirred into ice water and the aqueous solution is extracted several times with ether. The combined organic phases are dried and evaporated to dryness in vacuo. The resulting oil is used in the next stage without any further purification.

Yield: 187 g (88% of theory).

(b) 2-Methyl-2-propargyl-malonic acid 187 g (0.88 mol) of diethyl 2-methyl-2-propargyl-malonate are added to a solution of 101 g (1.8 mol) of potassium hydroxide in a mixture of 560 ml of water/ethanol (1:1) and the mixture is refluxed with stirring for 2 hours. After the reaction has ended (monitored by TLC) the mixture is evaporated to dryness in vacuo and the residue is then taken up with in water. The aqueous solution is acidified with 50% sulphuric acid and extracted several times with methylene chloride. The combined extracts are dried, evaporated to dryness in vacuo and a colourless product is obtained, m.p. 135° C.

Yield: 135 g (98% of theory).

(c) 2-Methyl-4-pentynoic acid 62.4 g (0.4 mol) of 2-methyl-2-propargyl-malonic acid are heated in an oil bath at 180° C. until the evolution of $CO_2$ has ended (about 30 minutes). A yellowish oil is obtained which is used directly in the next step.

Yield: 41 g (91.5% of theory).

(d) 2-Methyl-4-pentynoic acid chloride 40 g (0.36 mol) of 2-methyl-4-pentynoic acid are dissolved in 85 g of thionyl chloride and stirred for 24 hours at ambient temperature. Then the thionyl chloride is separated by distillation and the acid chloride obtained is used directly in the next step without further purification.

Yield: 46.8 g (100% of theory).

(e) 5,11-Dihydro-11-[1-oxo-2-methyl-4-pentynyl]-6H-pyrido[2,3-b][1,4]benzodiazepin-6-one At 0° to 10° C., with stirring, 416 ml (0.65 mol) of an n-butyl-lithium solution in n-hexane are added dropwise to a suspension of 63 g (0.3 mol) of 5,11-dihydro-6H-pyrido[2,3-b][1,4]benzodiazepin-6-one in 1500 ml of absolute tetrahydrofuran. THe mixture is stirred for a further hour at ambient temperature, then cooled to 5° to 10° C. and this temperature 46.8 g (0.36 mol) of 2-methyl-4-pentynoic acid chloride (not purified) dissolved in 100 ml of absolute tetrahydrofuran are added dropwise to the reaction solution. The mixture is stirred for a further 3 hours at ambient temperature, then added to 2000 ml of a saturated saline solution and diluted with about 2000 ml of ethyl acetate. The organic phase is separated off, extracted twice with 500 ml of saturated saline solution, dried over magnesium sulphate and evaporated to dryness in vacuo. The desired compound is obtained as a brownish-yellow product which is used without further purification in the next step.

Crude yield: 88 g (96% of theory).

A small sample was purified by column chromatography. M.p.: 202°–204° C. (ether).

Preparation of the end products

EXAMPLE 1

5,11-Dihydro-11-[1-oxo-6-(1-piperidinyl)-4-hexynyl]-6H-pyrido[2,3-b][1,4]benzodiazepin-6-one A mixture consisting of 9.6 g (0.03 mol) of 5,11-dihydro-11-[1-oxo-4-pentynyl]-6H-pyrido[2,3-b][1,4]benzodiazepin-6-one, 1.08 g (0.036 mol) of paraformaldehyde, 3.06 g (0.036 mol) of piperidine, 0.2 g of copper(I) chloride and 150 ml of dioxan is refluxed for 1 hour. After the reaction has ended the insoluble constituents are filtered off and the filtrate is evaporated to dryness in vacuo. The crude product is purified by column chromatography on silica gel (mobile phase: ethyl acetate, ethyl acetate + 10% methanol). After recrystallisation from ethyl acetate, 2.7 g (21% of theory) of the desired compound are obtained, m.p. 197° C.

EXAMPLE 2

5,11-Dihydro-11-[1-oxo-6-(1-pyrrolidinyl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and pyrrolidine in a yield of 41% of theory.
Melting point: 185°-186° C. (ethyl acetate).

EXAMPLE 3

5,11-Dihydro-11-[1-oxo-6-(hexahydro-1H-azepin-1-yl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and hexamethyleneimine in a yield of 24% of theory;
Melting point: 169°-170° C. (ethyl acetate).

EXAMPLE 4

5,11-Dihydro-11-[1-oxo-6-(4-methyl-1-piperazinyl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and 4-methyl-piperazine in a yield of 25% of theory;
M.p. 182°-183° C.

EXAMPLE 5

5,11-Dihydro-11-[1-oxo-6-[(methyl)(cyclohexyl)amino]-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and N-cyclohexyl-methylamine in a yield of 20% of theory;
M.p.: 162°-163° C. (ethyl acetate).

EXAMPLE 6

5,11-Dihydro-11-[1-oxo-6-(diethylamino)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and diethylamine in a yield of 16% of theory;
M.p.: 173°-174° C. (ethyl acetate)

EXAMPLE 7

5,11-Dihydro-11-[1-oxo-6-(4-trans-hydroxy-1-piperidinyl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and 4-hydroxy-piperidine in a yield of 30% of theory;
M.p.: 175°-176° C.

EXAMPLE 8

5,11-Dihydro-11-[1-oxo-6-[[2-(diethylamino)methyl]-1-piperidinyl]-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and 2-[(diethylamino)methyl]piperidine in a yield of 14% of theory;
M.p.: 157°-158° C. (ethyl acetate).

EXAMPLE 9

5,11-Dihydro-11-[1-oxo-6-[(methyl)(4-trans-hydroxycyclohexyl)amino]-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and N-(4-trans-hydroxy)cyclohexyl-methylamine in a yield of 27% of theory; M.p.: 176°-178° C. (ethyl acetate).

EXAMPLE 10

5,11-Dihydro-[1-oxo-6-(4-trans-hydroxy-hexahydro-1H-azepin-1-yl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and 4-hydroxyhexamethyleneimine in a yield of 16% of theory;
M.P.: 140°-141° C.

EXAMPLE 11

5,11-Dihydro-11-[1-oxo-6-[(methyl)(benzyl)amino]-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and N-benzyl-methylamine in a yield of 11% of theory;
M.p.: 204°-206° C. (ethyl acetate).

EXAMPLE 12

5,11-Dihydro-11-[1-oxo-6-(4-isopropyl-1-piperazinyl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and 4-isopropyl-piperazine in a yield of 10% of theory;
M.p.: 124°-126° C. (diisopropylether/ethyl acetate).

EXAMPLE 13

5,11-Dihydro-11-[1-oxo-6-(4-benzyl-1-piperazinyl)-4-hexynyl]-6H-pyrido[2,3-b][1,4]benzodiazepin-6-one Prepared analogously to Example 1 from 5,11-dihydro-11-[1-oxo-4-pentynyl]-6H-pyrido[2,3-b][1,4]benzodiazepin-6-one and 4-benzyl-piperazine in a yield of 21% of theory;

M.p.: 157°–158° C. (ethyl acetate).

EXAMPLE 14

5,11-Dihydro-11-[1-oxo-2-methyl-6-(1-pyrrolidinyl)-4-hexynyl]-6H-pyrido[2,3-b][1,4]benzodiazepin-6-one Prepared analogously to Example 1 from 5,11-dihydro-11-[2-methyl-1-oxo-4-pentynyl]-6H-pyrido[2,3-b][1,4]-benzodiazepin-6-one and pyrrolidine in a yield of 52% of theory;

M.p.: 158° C. (ethyl acetate).

EXAMPLE 15

5,11-Dihydro-11-[[[4-(1-piperidinyl)-2-butynyl]amino]carbonyl]-6H-pyrido[2,3-b][1,4]benzodiazepin-6-one Prepared analogously to Example 1 from 5,11-dihydro-11-[[(2-propynyl)amino]carbonyl]-6H-pyrido[2,3-b][1,4]benzodiazepin-6-one and piperidine in a yield of 44% of theory;

Melting point: 199°–200° C. (ethyl acetate/ethanol).

EXAMPLE 16

5,11-Dihydro-11-[[[4-(hexahydro-1H-azepin-1-yl)-2-butynyl](methyl)amino]carbonyl]-6H-pyrido[2,3-b][1,4]benzodiazepin-6-one Prepared analogously to Example 1 from 5,11-dihydro-11-[[N-methyl(2-propynyl)amino]carbonyl]6H-pyrido[2,3-b][1,4]benzodiazepin-6-one and hexamethyleneimine in a yield of 26% of theory;

M.p.: 145°–146° C. (ether).

EXAMPLE 17

5,11-Dihydro-11-[[[4-(1-piperidinyl)-2-butynyl]oxy]carbonyl]-6H-pyrido[2,3-b][1,4]benzodiazepin-6-one Prepared analogously to Example 1 from 5,11-dihydro-11-[[2-propynyl)oxy]carbonyl]-6H-pyrido[2,3-b][1,4]benzodiazepin-6-one and piperidine in a yield of 22% of theory;

M.p.: 207°–208° C. (decomposition).

EXAMPLE 18

5,11-Dihydro-11-[1-oxo-2-methyl-6-(4-methyl-1-piperazinyl)-4-hexynyl]-6H-pyrido[2,3-b][1,4]benzodiazepin-6-one A reaction mixture consisting of 36.6 g (0.12 mol) of 5,11-dihydro-11-[1-oxo-2-methyl-4-pentynyl]-6H-pyrido[2,3-b][1,4]benzodiazepin-6-one, 4 g (0.13 mol) of paraformaldehyde, 13.2 g (0.13 mol) of N-methylpiperazine, 0.2 g of copper(I) chloride and 600 ml of dioxan is refluxed for 2 hours. After the reaction has ended the mixture is filtered over activated charcoal to remove the insoluble components and the filtrate is evaporated to dryness in vacuo. In order to purify it, the crude product is suspended in a solution of 15.4 g (0.13 mol) of maleic acid in 600 ml of water and stirred for 1 hour at ambient temperature. The insoluble matter is filtered off, the filtrate is made alkaline by the addition of potassium carbonate and the resin precipitated is taken up in 600 ml of methylene chloride. After drying over magnesium sulphate, the solution is evaporated to dryness in vacuo. The crystalline residue is decocted with 150 ml of ethyl acetate and suction filtered after cooling. By digesting it in a little ethyl acetate a crystalline product is obtained which melts at 212° to 214° C. after washing with ether.

Yield: 30.5 g (60.9% of theory).

EXAMPLE 19

5,11-Dihydro-11-[1-oxo-2-methyl-6-(4-methyl-1-piperazinyl)-4-hexynyl]-6H-pyrido[2,3-b][1,4]benzodiazepin-6-one dihydrochloride 28 g (0.067 mol) of 5,11-dihydro-11-[1-oxo-2-methyl-6-(4-methyl-1-piperazinyl)-4-hexynyl]-6H-pyrido[2,3-b][1,4]benzodiazepin-6-one are suspended in 350 ml of absolute ethanol and 45 ml of ethereal hydrochloric acid are added with stirring at boiling temperature. A clear solution is obtained at first, which goes cloudy again after some time. A fine crystal slurry is precipitated which is cooled and suction filtered and then washed with 50 ml of absolute ethanol and 150 ml of acetone.

M.p.: 220°–221° C.

Yield: 32.5 g (98.9% of theory).

The preparation of pharmaceutical forms for administration will now be illustrated by some Examples:

EXAMPLE I

Tablets containing 5 mg of 5,11-dihydro-11-[1-oxo-6-(1-piperidinyl)-4-hexynyl]-6H-pyrido[2,3-b][1,4]benzodiazepin-6-one Composition:
1 tablet contains:

| | |
|---|---|
| Active substance | 50.0 mg |
| Lactose | 148.0 mg |
| Potato starch | 65.0 mg |
| Magnesium stearate | 2.0 mg |
| | 265.0 mg |

Method of preparation:

A 10% mucilage is prepared from potato starch by heating. The active substance, lactose and remaining potato starch are mixed together and granulated with the mucilage through a screen with a mesh size of 1.5 mm. The granulate is dried at 45° C., passed through the screen again, mixed with magnesium stearate and compressed to form tablets.

Weight of tablet: 220 mg
Die: 9 mm

EXAMPLE II

Coated tablets containing 5 mg of 5,11-dihydro-11-[1-oxo-6-(1-piperidinyl)-4-hexynyl]-6H-pyrido[2,3-b][1,4]benzodiazepin-6-one The tablets prepared according to Example I are coated in known manner with a coating consisting essentially of sugar and talc. The finished coated tablets are polished with beeswax.

Weight of coated tablet: 300 mg

EXAMPLE III

Ampoules containing 1 mg of 5,11-dihydro-11-[1-oxo-6-(1-piperidinyl)-4-hexynyl]-6H-pyrido[2,3-b][1,4]benzodiazepin-6-one Composition:
1 ampoule contains:

| | |
|---|---|
| Active substance | 10.0 mg |
| Sodium chloride | 8.0 mg |

| | | |
|---|---|---|
| -continued | | |
| Distilled water | ad | 1 ml |

Method of preparation:

The active substance and sodium chloride are dissolved in distilled water and then made up to the volume specified. The solution is filtered sterile and transferred into 1 ml ampoules.

Sterilisation: 20 minutes at 120° C.

EXAMPLE IV

Suppositories containing 5 mg of 5,11-dihydro-11-[1-oxo-6-(1-piperidinyl)-4-hexynyl]-6H-pyrido[2,3-b][1,4]benzodiazepin-6-one Composition:
1 suppository contains:

| | |
|---|---|
| Active substance | 50.0 mg |
| Suppository mass | 1695.0 mg |
| (e.g. Witepsol W 45 ®) | |
| | 1745.0 mg |

Method of preparation:

The finely powdered active substance is suspended in the molten suppository mass which has been cooled to 40° C. At 37° C. the mass is poured into slightly chilled suppository moulds.

Weight of suppository 1.7 g

EXAMPLE V

Drops containing 5,11-dihydro-11-[1-oxo-6-(1-piperidinyl)-4-hexynyl]-6H-pyrido[2,3-b][1,4]benzodiazepin-6-one Composition:
100 ml of drops solution contains:

| | | |
|---|---|---|
| Methyl p-hydroxybenzoate | | 0.035 g |
| Propyl p-hydroxybenzoate | | 0.015 g |
| Aniseed oil | | 0.05 g |
| Menthol | | 0.06 g |
| Pure ethanol | | 10.0 g |
| Active substance | | 5.0 g |
| Sodium cyclamate | | 1.0 g |
| Glycerol | | 15.0 g |
| Distilled water | ad | 100.0 ml |

Method of preparation:

The active substance and sodium cyclamate are dissolved in about 70 ml of water and glycerol is added. The p-hydroxybenzoates, aniseed oil and menthol are dissolved in ethanol and this solution is added to the aqueous solution with stirring. Finally, the mixture is made up to 100 ml with water and filtered to remove any suspended particles.

EXAMPLE VI

Tablets containing 50 mg of 5,11-dihydro-11-[1-oxo-2-methyl-6-(4-methyl-1-piperazinyl)-4-hexynyl]-6H-pyrido[2,3-b][1,4]benzodiazepin-6-one Composition:
1 tablet contains:

| | |
|---|---|
| Active substance | 50.0 mg |
| Lactose | 148.0 mg |

| | |
|---|---|
| -continued | |
| Potato starch | 65.0 mg |
| Magnesium stearate | 2.0 mg |
| | 265.0 mg |

Method of preparation:

A 10% mucilage is prepared from potato starch by heating. The active substance, lactose and remaining potato starch are mixed together and granulated with the mucilage through a screen with a mesh size of 1.5 mm. The granulate is dried at 45° C., passed through the screen again, mixed with magnesium stearate and compressed to form tablets.

Weight of tablet: 220 mg
Die: 9 mm

EXAMPLE VII

Coated tablets containing 50 mg of 5,11-dihydro-11-[1-oxo-2-methyl-6-(4-methyl-1-piperazinyl)-4-hexynyl]-6H-pyrido[2,3-b][1,4]-benzodiazepin-6-one The tablets prepared according to Example VI are coated in known manner with a coating consisting essentially of sugar and talc. The finished coated tablets are polished with beeswax.

Weight of coated tablet: 300 mg

EXAMPLE VIII

Ampoules containing 10 mg of 5,11-dihydro-11-[1-oxo-2-methyl-6-(4-methyl-1-piperazinyl)-4-hexynyl]-6H-pyrido[2,3-b][1,4]benzodiazepin-6-one dihydrochloride Composition:
1 ampoule contains:

| | | |
|---|---|---|
| Active substance | | 10.0 mg |
| Sodium chloride | | 8.0 mg |
| Distilled water | ad | 1 ml |

Method of preparation:

The active substance and sodium chloride are dissolved in distilled water and then made up to the volume specified. The solution is filtered sterile and transferred into 1 ml ampoules.

Sterilisation: 20 minutes at 120° C.

EXAMPLE IX

Suppositories containing 50 mg of 5,11-dihydro-11-[1-oxo-2-methyl-6-(4-methyl-1-piperazinyl)-4-hexynyl]-6H-pyrido[2,3-b][1,4]benzodiazepin-6-one Composition:
1 suppository contains:

| | |
|---|---|
| Active substance | 50.0 mg |
| Suppository mass | 1695.0 mg |
| (e.g. Witepsol W 45 ®) | |
| | 1745.0 mg |

Method of preparation:

The finely powdered active substance is suspended in the molten suppository mass which has been cooled to 40° C. At 37° C. the mass is poured into slightly chilled suppository moulds.

Weight of suppository 1.745 g

EXAMPLE X

Drops containing 5,11-dihydro-11-[1-oxo-2-methyl-6-(4-methyl-1-piperazinyl)-4-hexynyl]-6H-pyrido[2,3-b][1,4]benzodiazepin-6-one dihydrochloride Composition:

100 ml of drops solution contains:

| Methyl p-hydroxybenzoate | | 0.035 g |
|---|---|---|
| Propyl p-hydroxybenzoate | | 0.015 g |
| Aniseed oil | | 0.05 g |
| Menthol | | 0.06 g |
| Pure ethanol | | 10.0 g |
| Active substance | | 5.0 g |
| Sodium cyclamate | | 1.0 g |
| Glycerol | | 15.0 g |
| Distilled water | ad | 100.0 ml |

Method of preparation:

The active substance and sodium cyclamate are dissolved in about 70 ml of water and glycerol is added. The p-hydroxybenzoates, aniseed oil and menthol are dissolved in ethanol and this solution is added to the aqueous solution with stirring. Finally, the mixture is made up to 100 ml with water and filtered to remove any suspended particles.

What is claimed:

1. A 5,11-dihydro-6H-pyrido[2,3-b][1,4-benzodiazepin-6-one of the formula I

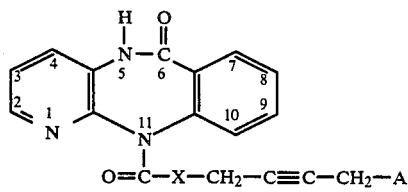

wherein

X is one of the groups

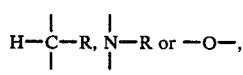

and

A is one of the groups

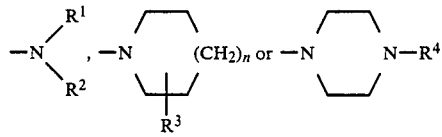

wherein

R is a hydrogen atom or an alkyl group with 1 to 3 carbon atoms, $R^1$ and $R^2$, which may be identical or different, are each a hydrogen atom, an alkyl group with 1 to 3 carbon atoms, a phenylalkyl group with a total of 7 to 9 carbon atoms or a 5 to 7 membered cycloalkyl group optionally substituted by a hydroxy group, n is 0, 1 or 2, $R^3$ is a hydrogen atom, a hydroxy group, an alkyl group with 1 to 3 carbon atoms or a group of formula

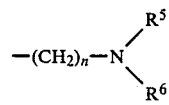

wherein n is defined as hereinbefore, and $R^5$ and $R^6$ are each an alkyl group with 1 to 3 carbon atoms, and $R^4$ is a straight-chained or branched alkyl group with 1 to 3 carbon atoms or a phenylalkyl group with a total of 7 to 9 carbon atoms, or a pharmaceutically acceptable salt thereof.

2. 5,11-Dihydro-11-[1-oxo-2-methyl-6-(4-methyl-1-piperazinyl)-4-hexynyl]-6H-pyrido][2,3-b][1,4]benzodiazepin-6-one or a pharmaceutically acceptable salt thereof.

3. 5,11-Dihydro-11-[1-oxo-6-(1-piperidinyl)-4-hexynyl]-6H-pyrido[2,3-b][1,4]benzodiazepin-6-one or a pharmaceutically acceptable salt thereof.

4. 5,11-Dihydro-11-[1-oxo-6-(hexahydro-1H-azepin-1-yl)-4-hexynyl]-6H-pyrido[2,3-b][1,4]benzodiazepin-6-one or a pharmaceutically acceptable salt thereof.

5. A pharmaceutical composition useful for treating thromboebolic disease, bradycardia or bradyarrythmia containing an effective amount of a compound of Formula I, as claimed in claim 1, together with conventional carriers and/or excipients.

6. In accordance with claim 5, a pharmaceutical composition containing 5,11-dihydro-11-[1-oxo-2-methyl-6-(4-methyl-1-piperazinyl)-4-hexynyl]-6H-pyrido[2,3-b]-[1,4]benzodiazepin-6-one of a pharmaceutically acceptable salt thereof together with conventional excipients and additives.

7. A method for treating thromboembolic disease which comprises administering, to a subject in need thereof, an anti-thrombotic amount of 5,11-dihydro-11-[1-oxo-2-methyl-6-(4-methyl-1-piperazinyl)-4-hexynyl]-6H-pyrido[2,3-b][1,4]benzodiazepin-6-one or a pharmaceutically acceptable salt thereof.

8. A method for treating bradycardia or bradyarrythmia which comprises administering to a subject suffering from the same a heart rate elevating amount of a compound according to claims 1, 2, 3, or 4.

* * * * *